United States Patent [19]
Roux et al.

[11] Patent Number: 5,908,697
[45] Date of Patent: Jun. 1, 1999

[54] ACTIVE PRINCIPLE CARRIERS CONTAINING NON-IONIC SURFACTANTS, AND USES THEREOF, PARTICULARLY IN FOOD, COSMETICS AND PHARMACEUTICALS

[75] Inventors: Didier Roux, Merignac; Corinne Degert, Saint-Medard-en-Jalles; René Laversanne, Pessac, all of France

[73] Assignee: Capsulis, Pessac, France

[21] Appl. No.: 08/983,515

[22] Filed: Dec. 8, 1997

Related U.S. Application Data

[63] Continuation of application No. PCT/FR96/00958, Jun. 20, 1996.

[30] Foreign Application Priority Data

Jun. 21, 1995 [FR] France .................................. 95 07398

[51] Int. Cl.⁶ ...................................................... A23P 1/04
[52] U.S. Cl. ................................ 428/402.2; 428/402.21; 428/402.22; 428/402.24
[58] Field of Search .......................... 428/402.2, 402.21, 428/402.22, 402.24

[56] References Cited

U.S. PATENT DOCUMENTS 4,217,344  8/1980  Vanlerberghe et al. .

FOREIGN PATENT DOCUMENTS

| A-87993 | 9/1983 | European Pat. Off. . |
| A-489207 | 6/1992 | European Pat. Off. . |
| A-4421686 | 5/1995 | Germany . |
| WO-A-9319735 | 10/1993 | WIPO . |
| WO 95/19707 | 7/1995 | WIPO . |

Primary Examiner—Nathan M. Nutter
Attorney, Agent, or Firm—Merchant, Gould, Smith, Edell, Welter & Schmidt

[57] ABSTRACT

Novel active principle carriers containing non-ionic surfactants are disclosed. The surfactants mainly consist of sucrose and fatty acid esters and form onion-structured microcapsules within which the active material is encapsulated. Compositions suitable for use as food, diet food, cosmetics or pharmaceuticals, containing at least one active materiel or additive encapsulated in said microcapsules, are also disclosed.

26 Claims, 1 Drawing Sheet

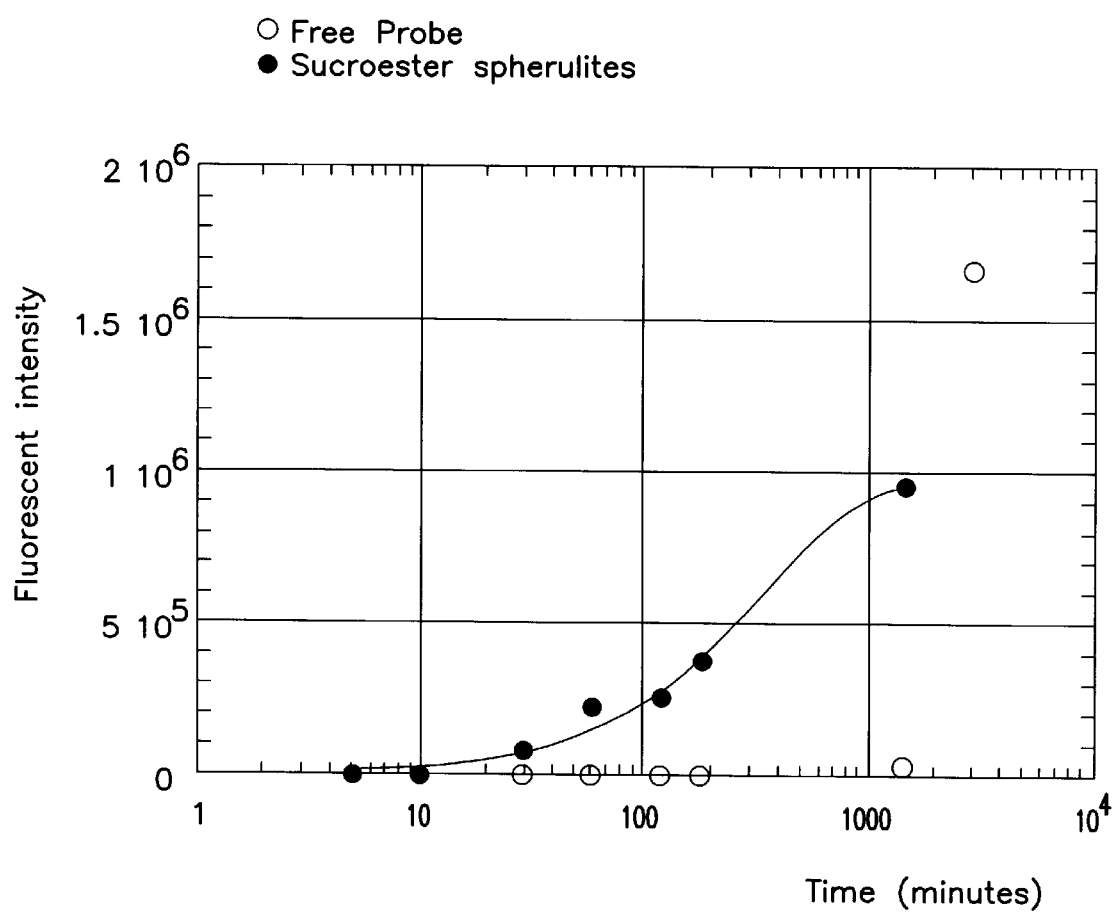

ACTIVE PRINCIPLE CARRIERS CONTAINING NON-IONIC SURFACTANTS, AND USES THEREOF, PARTICULARLY IN FOOD, COSMETICS AND PHARMACEUTICALS

This application is a continuation filed under 35 USC 371 of PCT/FR96/00958, filed Jun. 20, 1996.

BACKGROUND OF THE INVENTION

The invention relates to active principle carriers based on non-ionic surfactants and their applications notably in food, cosmetic and pharmaceutical fields.

The invention also relates to compositions in which at least one active principle is encapsulated within this carrier, in particular compositions for use as food, cosmetics or pharmaceuticals and their method of manufacture.

It is known that there is a significant necessity, in these fields, to protect a certain number of fragile or volatile molecules or to regulate the conditions of their release into an external medium.

One of the techniques which enables attaining such an aim is the microencapsulation of active molecules. The aim of this encapsulation is to reduce the evaporation and the transfer towards the environment of the active material, either during storage or during the development of the products, or even during their consumption.

The invention can also enable rendering the material easier to use by diluting it and by favouring its homogeneous distribution within the support.

The list of sensitive materials is long. Amongst the most used, acids, for example ascorbic acid or lactic acid, colouring agents, for meats in particular, lipids, vitamins, flavours and essential oils, enzymes, will be cited for example in the food field.

In the cosmetic or pharmaceutical field, dihydroxyacetone, vitamins, phenolic oligomers, biomolecules, can be cited. Some of the active products cited in foods are also useful in cosmetics or in pharmaceuticals.

The technologies, currently used in order to attain this object rely on the use of polymers. These are techniques either of coacervation, extrusion or coating by fluidised bed.

Apart from the dispersing effect, the surfactant molecules enable, in certain cases, protecting and vectorising and then releasing the active molecules in a controlled manner using microcapsules formed by a supramolecular combination of surfactant molecules. The most common example is that of liposomes used in cosmetics and in the biomedical field. These liposomes correspond to an arrangement of unilamellar or multilamellar vesicles of sizes between a few hundred Angströms and several microns. These vesicles are, in the case of liposomes, obtained from phospholipidic molecules (extracted for example from soya or egg). These liposomes are capable of encapsulating hydrophilic or even lipophilic active molecules and thus carrying out the functions of vectoring and release sought after.

The classical methods of preparation of the liposomes most often necessitate the presence of an organic co-solvent or alcohols, products which are strongly advised against for applications in the field of food and which are to be prevented in the other fields more particularly covered by the present invention.

However, in the field of the food industry, tests carried out with lecithins, in particular in the form of liposomes, have shown the technological limitations of this technique. The use of liposomes in the food industry is in fact limited by the process of manufacture which has a certain number of technical problems. More specifically, the use of liposomes in the food industry has the drawback of leading to a low yield of encapsulation and this despite a relatively heavy and therefore expensive technology to carry out.

The U.S. Pat. No. 4,217,344 describes a process which enables producing a dispersion of spheres which comprises an arrangement of molecular layers encapsulating an aqueous phase. The process described in this document consists in mixing a water-dispersible lipid compound with the aqueous phase to be encapsulated, the lipophilic/hydrophilic ratio of the lipid compound being such that the liquid swells in the aqueous phase to form a lamellar phase which is then submitted to a stirring step.

Amongst the lipid compounds cited in this document, compounds are found essentially of the polyglycerol ether type synthesised specifically for forming vesicles.

A novel family of surfactants of the ether type has now been found which enables obtaining stable vesicles which allow encapsulating active principles.

A more particular advantage of the surfactants selected according to the invention is that they are natural, biodegradable non-ethoxylated products which are easily obtained commercially and which thus enable obtaining multilamellar microvesicles from commercial surfactants, without having to carry out a particular synthesis.

The liposomes or other lipid vesicles described in the literature are in fact hitherto based essentially on surfactants:

—ionic or zwitterionic surfactants, as is the case of lecithin and its derivatives, or sodium dodecylsulphate (SDS), —non-ionic ethoxylated surfactants, as is the case of sorbitan ester-based microcapsules, —non-ionic surfactants specially synthesised to give vesicles.

The use of these products has certain drawbacks, amongst others, in the fields of cosmetics and food:

—irritation in the case of ionic surfactants and certain non-ionic ethoxylated surfactants, —risk of allergy due to the traces of ethylene oxide in the ethoxylated products, —great sensitivity to microbial contamination as far as lecithin and ethoxylated products which inhibit preservatives are concerned, —chemical instability as far as lecithin is concerned, —specificity of formulation.

SUMMARY OF THE INVENTION

The non-ionic surfactants used according to the invention are essentially constituted of fatty acid esters and of sucrose, optionally in a mixture with glycerol esters. Advantageously, they are derivatives of natural products preferably of plant origin which enable preventing the drawbacks of the products cited above. They have not been used hitherto for the preparation of lipid vesicles which are based principally on lecithin, non-ionic ethoxylated surfactants or non-ionic surfactants which necessitate a specific synthesis.

Above all, these surfactants have hitherto been developed for the food industry since they are very well tolerated, do not present a risk of allergy nor of transmission of disease of animal origin. On the other hand, they generally give a very soft structure and a pleasant touch to the cosmetic preparations in which they have been introduced. Furthermore, by virtue of their good compatibility with the skin, they favour the penetration of the cosmetic active principles.

These surfactants have proved to be particularly interesting for the preparation of multilamellar vesicles used as vectors for active principles, both for the food industry and for the cosmetic or pharmaceutical industry. They possess a variety of significant physico-chemical properties which enable selecting from them couples of different properties (high and low HLB) in order to correctly formulate the lamellar liquid-crystal phase necessary for obtaining microvesicles, as will appear from the description that follows.

They are also known to reduce the cytotoxic effects and therefore irritant or allergy forming effects of other surfactants, in particular ionic surfactants.

Finally, they are less sensitive to bacterial contamination, and possess even for some, in particular as far as sucroesters are concerned, bacteriostatic properties. From this, these surfactants can not only be used in a mixture together for forming multilamellar microvesicles of surfactants, but they can also be used to supplement other surfactants in order to obtain the properties necessary for the formulation, while at the same time reducing the drawbacks of these other surfactants (irritation of the ionic surfactants, contamination of lecithins . . . ).

BRIEF DESCRIPTION OF THE DRAWINGS

The drawing illustrates the relationship between fluorescent intensity and the passage of time for Example 19, showing the ability of a product of the present invention to cross a reconstructed human epidermis.

DETAILED DESCRIPTION

The vesicles according to the invention can be obtained in a particularly simple way by formation of a lamellar liquid-crystal phase and by causing the rearrangement of the bi-layers formed in order to form microcapsules. A process of this type enabling making microcapsules of controlled size is described in the International Application WO 93/19735 which describes a process which enables, by virtue of a recourse to a step of shearing of a lamellar liquid-crystal phase, preparing microcapsules of controlled size, not only from lipid surfactants which can form liposomes, but also from various anionic or non-ionic surfactants, and proposes the encapsulation of substances, notably biological substances, in these capsules.

The International Application WO 95/19707 itself describes a process intended to improve the remanence of an odour and consisting in encapsulating an odoriferous active principle within a microcapsule constituted of a multilamellar arrangement of concentric bi-layers separated by an aqueous medium. These microcapsules are obtained by preparing a liquid-crystal phase or a suspension of liquid-crystal phase from at least one surfactant addition and by causing the rearrangement of the bi-layers in the form of microcapsules. This rearrangement can be in particular obtained by using the process described in the International Application WO 93/19735.

The vesicles according to the invention can be obtained by a process derived directly from those described in the International Applications WO 95/19707 or WO 93/19735.

According to the invention, the active product that is desired to protect or the release of which is desired to be controlled from a composition is incorporated almost totally inside the multilamellar vesicles that will be designated in the present text equally by microcapsules, microvesicles or vesicles. These microcapsules are advantageously roughly spherical and are constituted of concentric lamellae which gives them an "onion" type structure.

The active substance is thus found included within the microcapsule itself, generally in its membranes, if need be in the interstitial water included inside the microcapsule if it is purely hydrophilic. However, it is always an integral part of the microcapsule.

Such an encapsulation enables one to ensure the functions of dispersability and/or vectoring and controlled release of the encapsulated product.

Even if, in general terms, water/surfactant(s) media are used for preparing the microcapsules of the invention, it is in no way excluded to replace the water by a polar solvent, glycerol for example.

According to a first advantage, the process of the invention enables one to use, in order to carry out the encapsulation, a variety of surfactants which are perfectly compatible with the uses sought after, in particular with the uses in the fields of food, cosmetics or pharmaceuticals, notably in the dermatological field.

According to another advantage, the technology proposed according to the invention allows the preparation of vesicles having a very high encapsulation yield, notably a yield greater than 90% and generally very close to 100%. Due to its easy use, this technology also enables the preparation of large amounts of encapsulated products. Moreover, the technology does not make use of an organic co-solvent, this enables envisaging the industrial use of the multilamellar vesicles for microencapsulating molecules or compositions with a specific use.

Another advantage comes from the fact that the use of the surfactants gives a good dispersability to the formulation which can be used as a liquid in an aqueous dispersion. This aspect is particularly advantageous when one is concerned with hydrophobic or water-insoluble molecules which can be dispersed by virtue of the invention without having recourse to an organic solvent.

Furthermore, the classical techniques of microencapsulation, in particular of flavours, consists in coating the lipophilic product with a polymerised shell. This leads to encapsulated flavours which are released at once upon the splitting of the shell. Similarly, the techniques of molecular encapsulation, by cyclodextrin for example, lead to a permanent complex and to a real chemical equilibrium between the complexed form and the free form. In contrast, the technology of microencapsulation by surfactants according to the invention enables an appreciably different release. It may in fact be considered that the active product, for example the flavour, constantly leaks but the release of the active product is considerably slowed down compared to the same product free.

Furthermnore, due to their small size, in the order of a micrometer, these capsules are generally not destroyed during the mastication process, which enables, in the case of food products, a particularly pronounced remanence of the sensation linked to the taste of the product throughout the whole mastication period.

Further still, this technology enables in certain cases increasing the availability of a lipophilic flavour. In fact, if a lipophilic flavour is mixed in a medium itself lipophilic, its availability in the mouth (aqueous medium) can be very limited. The flavour is in this case trapped in its medium and is not released. This is the case for example of flavours dispersed in a milk product or in the fatty parts of meat or even in the polymer matrix of a chewing gum.

According to one of its aspects, the present invention provides a process which enables protecting, before their introduction into compositions for a specific use, in particular food, cosmetic or pharmaceutical, notably dermatological use, products or additives that are fragile and/or that the release of which is desired to control, in particular during their consumption. This process consists in encapsulating these products or additives inside multilamellar vesicles constituted of specific surfactants used according to the invention.

According to another aspect, the invention relates to an active substance carrier constituted of vesicles based on well-determined ester-type non-ionic surfactants.

According to another aspect, the invention relates to compositions for specific use in which the active substance is included in the vesicles of the invention.

More specifically, the invention relates to compositions for use as food or diet food in which a product or an additive for use as food or diet food is microencapsulated.

The invention also relates to pharmaceutical compositions in which at least one active substance is included in the vesicles prepared according to the invention.

The invention also relates to cosmetic compositions in which at least one cosmetically effective active principle is included in the vesicles according to the invention.

The invention also relates, according to another aspect, to foodstuffs incorporating an encapsulated product or an additive for food use.

The invention also relates, and this insofar as to the use of surfactants of the family of sucroesters and sucroglycerides are described for the first time for preparing microcapsules constituted of a multilamellar arrangement of concentric bi-layers, to the use of these particular surfactants for preparing such microcapsules and this independent of the nature of the active principle encapsulated, and the use sought after.

Such compositions which contain microcapsules based on sucroglycerides and/or sucroesters will more particularly be able to be used in the field of cosmetology. In fact, the surfactants cited above have the advantage in being particularly not very irritant and in giving a very soft texture to the products in which they are used. Used in the microcapsules, they give access to vectors of efficient and particularly well-tolerated active principles, useful both in dermocosmetology and in dietetics.

Thus, according to one of its essential characteristics, the invention relates to an active principle carrier in the form of multilamellar vesicles constituted of concentric membranes, characterised in that said membranes comprise at least one non-ionic surfactant of the sucrose ester type comprising at least one chain arising from a linear or branched, saturated or unsaturated, optionally mono- or polyhydroxylated $C_{12}$ to $C_{22}$ fatty acid.

The fatty acids entering into the composition of the surfactants used for preparation of the vesicles according to the invention can be any $C_{12}$ to $C_{22}$ fatty acid cited above. However, fatty acids of natural origin, preferably of plant origin will advantageously be chosen, more specifically those found in vegetable oils. It may be either a defined fatty acid or a mixture of fatty acids, in particular mixtures derived from a natural oil, in particular olive oil, groundnut oil, rapeseed oil, castor oil, palm oil, coconut oil, sesame oil. These fatty acids can be partially or totally hydrogenated. It will be possible in particular to use different fatty acids found in a mixture in varying proportions in the oils cited above and constituted essentially of saturated, mono-unsaturated or poly-unsaturated $C_{12}$ to $C_{22}$ fatty acids.

According to a variant of the invention, the ester-type surfactant used according to the invention is a mixed ester which comprises, in addition to the chains originating from the fatty acids cited above, at least one chain originating from a carboxylic acid with a relatively short chain. These chains originate from saturated or unsaturated, hydroxylated or non-hydroxylated $C_2$ to $C_4$ mono- or polyacids, the hydroxyl function(s) being free or esterified by carboxylic acid acid. As examples of such acids, acetic acid, lactic acid, citric acid, tartaric acid, acetyltartaric acid, succinic acid will be cited.

According to another variant of the invention, the surfactants defined above can be used in a mixture with glyceride-type surfactants, this mixture constituting what is customarily referred to as "sucroglycerides". The sucroglycerides used according to the invention can be any sucroglyceride which can be obtained by partial transesterification of a mono-, di- or triglyceride of a $C_{12}$ to $C_{22}$ fatty acid as defined above with sucrose.

In addition to the surfactants defined above, it will be possible for the vesicles according to the invention to contain at least one surfactant such as lecithin, a sorbitan ester or a polysorbate.

The carrier according to the invention is more specifically constituted of microcapsules constituted of a multilamellar arrangement of concentric bi-layers constituted of at least one surfactant and separated by a medium constituted of a polar liquid known as interstitial solvent, the active product being included in the membranes of said microcapsules and/or in the interstitial solvent of said microcapsules.

According to a particularly advantageous variant of the invention, the polar liquid is constituted of water and the active product or additive is included in the membranes of said microcapsules when it is hydrophobic and/or in the interstitial solvent when it is hydrophilic.

The microcapsules contained in the compositions above are advantageously of dimensions between 0.1 and 50 $\mu$m, preferably between 0.2 and 10 $\mu$m.

These microcapsules can be observed with an optical microscope. They are advantageously of a size preferably of the order of a micrometer. It is due to this small size that the microcapsules are submitted to Brownian motion and do not undergo or undergo very little separation or frothing in aqueous solution, which is a more particular advantage of the invention.

As it has been seen above, the microcapsules of the invention have a multilamellar structure, i. e. an onion structure constituted of a succession of concentric layers of surfactants.

For the preparation of the microcapsules useful according to the invention, surfactants which are compatible with a use in the field sought after are preferably chosen.

For the implementation of the process of the invention which will be described further on, at least two surfactants of which one at least, and, preferably at least two, is a surfactant of the sucroester type such as defined above or a mixture containing same, in particular a sucroglyceride, are selected advantageously for use. More specifically, when a mixture of two surfactants is used, a mixture is selected preferably comprising a first surfactant known as lipophilic agent having a hydrophilic-lipophilic balance (HLB)

between 3 and 7 and a second surfactant known as hydrophilic agent having an HLB between 8 and 15, at least one of these two surfactants belonging to the family of sucroglycerides or sucroesters such as defined above.

In this case, at least one surfactant will preferably be chosen which has a critical micellar concentration (CMC) lower than $10^{-5}$ mole/l, preferably lower than $10^{-6}$ mole/l.

The proportion of lipophilic surfactant in the membrane is, expressed in percentage by weight with respect to the whole of the surfactants, between 0% and 100%, preferably between 20% and 100%, the remainder being constituted of hydrophilic surfactant.

According to a particularly advantageous variant, at least one of the surfactants, and preferably the two lipophilic surfactants, is selected from the group consisting of:
—esters of sucrose and linear or branched, saturated or unsaturated, optionally mono- or polyhydroxylated $C_{12}$ to $C_{22}$ fatty acids,
—mono-, di- and triesters of glycerol of the same fatty acids,
—mixed esters of glycerol of the same fatty acids and saturated or unsaturated, hydroxylated or non-hydroxylated $C_2$ to $C_4$ mono- or poly-acids, the hydroxyl function(s) being free or esterified by a carboxylic acid, for example acetic acid, lactic acid, citric acid, tartaric acid, acetyltartaric acid, succinic acid,
—sucroglycerides formed from a mixture of esters of sucrose and mono- or diglycerides prepared with the same fatty acids.

As hydrophilic surfactant, any hydrophilic surfactant such as defined above will be chosen.

The family of the sucroester-type surfactants will be particularly preferred.

Fatty acid sucroesters derived from vegetable fats will preferably be chosen.

Generally, the surfactants according to the invention will advantageously contain simple or mixed esters or mixtures of fatty acid esters selected independently preferably from lauric acid, myristic acid, palmitic acid, stearic acid, behenic acid, oleic acid, linoleic acid, linolenic acid, arachidonic acid, ricinoleic acid and their mixtures.

The vesicles described above can be strengthened by coating by means of a polymer, advantageously a polymer of natural, vegetable or marine origin, or co-encapsulation of such a polymer with the active principle. Such a coating or such a co-encapsulation enables conserving the specific features of the vesicles according to the invention, namely the features of tolerance, softness and compatibility of the surfactants described.

The polymers advantageously used for coating the vesicles or to be co-encapsulated with an active principle so as to strengthen said vesicles are advantageously selected from the following classes of polymers:
—natural or modified, linear or substituted, neutral or ionic polysaccharides, in particular guar gums, locust bean gums, gum arabic, carrageenans (kappa, iota and lambda), xanthan gums, natural, esterified or amidated pectins, alginic acid and its salts, hyaluronic acid, quaternised guar gums, chitosan and its substituted derivatives,
—gelatine,
—hydro- or liposoluble synthetic polymers such as polyacrylamide, polyvinylpyrrolidone, poly(ethylene glycol).

As has been set forth above, the invention also relates to various compositions which use the vesicles described above as active principle carrier. In particular, these are compositions for use as food or diet food, pharmaceutical compositions or cosmetic compositions.

The products or additives for use as food or diet food, that are encapsulated according to the invention are all products known as additives for food use, known for their fragility. They can also be products of hydrophilic character as well as hydrophobic character.

As examples of products for use as food that will be encapsulated according to the present invention, acid-type products for use as food, will be cited in particular, notably ascorbic acid or lactic acid, colouring agents, in particular colouring agents for meat, lipids, vitamins, food flavours, essential oils, enzymes.

When the food active principle is of hydrophilic character, its concentration in the capsule, expressed in percentage by weight with respect to the total weight of the capsule, including the weight of the polar liquid, the surfactant(s) and the encapsulated active principle, is generally between 5 and 30%, preferably between 10 and 20%. When the active product is hydrophobic, its concentration in the capsule is generally between 5 and 30%, preferably between 5 and 20%.

The invention also relates to cosmetic compositions in which an active agent, in particular an active agent whose penetration across the skin is desired to be improved, is included inside the vesicles described above.

The invention also relates to pharmaceutical compositions which contain at least one active agent included inside the vesicles such as described above, in particular an active agent the release of which is desired to be improved or control or, more particularly, in the case of the compositions for dermnatological use, an active agent whose penetration across the skin is desired to be improved.

As examples, hydrating active agents can be cited, or anti-free-radicals for cosmetics, anti-inflammatories, local anaesthetics, anti-allergics, analgesics for pharmacy.

In the cosmetic or pharmaceutical compositions, the concentrations of active principle can vary considerably with the nature of this active principle. In general, they are between 5 and 60% with respect to the total weight of the capsule. The relatively high percentages, for example from 50 to 60% can, in particular, be used when the active principle replaces the interstitial water; this is for example the case of glycerol used as hydrating agent in cosmetics.

According to another of its aspects, the invention also relates to a method of preparation of the compositions described above. This method consists in preparing a lamellar liquid-crystal phase which contains at least one surfactant of the sucroester type as defined above, a polar solvent, advantageously constituted of water, and the product or the composition that is desired to encapsulate and to cause the rearrangement of said liquid-crystal phase in the form of multilamellar vesicles.

More specifically, the preparation technique consists, in a first step, of preparing a lamellar liquid-crystal phase which contains a mixture of the surfactant(s), the polar solvent, preferably water, and the active product or mixture that is desired to encapsulate.

In order to optimise the encapsulation yield, conditions will be chosen such as the liquid-crystal phase should be homogeneous, i. e. mono-phase, such that the whole of the polar solvent (water in general), the whole of the active product or mixture be dissolved in this lamellar phase.

It will be possible for the optimal conditions to be used to be generally determined by an inspection, of a series of compositions which contain varying amounts of solvent and active product. This inspection will be made either by microscopic observation by observing the phase separation, or by microscopic observation using an optical microscope, preferably a polarising microscope.

However, the formation of a liquid-crystal phase is not a condition which is sufficient to obtain, in what follows, an organisation of this lamellar phase in the form of a compact stacking of these vesicles. It will be possible for this rearrangement to be obtained by applying a homogeneous shearing, as described in the patent application WO 93/19735. It will also be possible for this rearrangement to be obtained by adjusting the particular formulation of the mixture, in particular by selecting a mixture of surfactants, so that the texture sought after, in the form of multilamellar vesicles, form spontaneously or, failing that, during a simple mechanical treatment, for example during the mixing of the products which cause such a mechanical treatment.

This is the reason why a mixture of surfactants and respective concentrations of each one of the surfactants contained in this mixture will advantageously be chosen such that a desired texture be obtained.

More specifically, a mixture of surfactants will be used which is in general constituted of two types of surfactants, one being rather soluble in water and having therefore a high HLB, and the other being rather soluble in oil and having therefore a relatively low HLB. Furthermore, it will be particularly advantageous that at least one of the surfactants have a relatively low CMC, preferably lower than $10^{-5}$ mole/liter, preferably even lower than $10^{-6}$ mole/l.

The proportion by weight of the surfactants in the final mixture is generally between 5 and 90%, preferably between 30 and 70%.

More specifically, in order to obtain the microcapsules sought after, starting mixtures will be used which have the following properties:

1) The mixture must form a homogenous liquid-crystal lamellar phase for proportions of water, by weight, ranging from 10 to 98%, more generally from 20 to 60%.

2) This homogeneous lamellar phase must possess a specific texture, i. e. a spatial arrangement of the lamellae which, either spontaneously or by simple mixing, or even under the action of a specific shearing such as described in the International Application WO 93/19735, corresponds to an "onion" structure. This structure can easily be recognised by the person skilled in the art by using a polarising microscope.

In order to obtain the two conditions above, two surfactants, as explained above, will advantageously be used having appreciably different hydrophilic/lipophilic equilibria, so as to be thus able to regulate at will the properties of organisation (texture) of the lamellar phase.

A surfactant which is rather lipophilic will preferably be selected to be mixed having a low HLB between 3 and 7 and a hydrophilic surfactant having a high HLB between 8 and 15. The person skilled in the art will be easily able to vary the proportions of the two types of surfactant, to obtain a homogeneous lamellar phase having the property of texture sought after.

The two types of surfactant will be selected from the surfactants compatible with the use sought after.

Thus, the lipophilic type surfactant will advantageously be selected from the family comprising mono-, di- and triglycerides or their derivatives, in particular their derivatives of the ester type and the sucroglycerides.

The hydrophilic type surfactant will particularly advantageously be selected from the family of sucroesters.

In certain particular cases, these capsules can be obtained from a single commercial product. This is the case of the product marketed by Rhône-Poulenc under the name of celynol PPH, which is a hydrogenated sucroglyceride.

By applying the process of preparation described above, two types of capsules are achieved according to the degree of organisation of the surfactant molecules in the membrane which constitute the compartments of the multilamellar vesicles:

—the vesicles of the "fluid" type correspond to the membranes wherein the surfactant molecules are free to move around and are not organised in the form of a bidimensional crystalline network. They are in general spherical.

—in contrast, the "solid" type vesicles correspond to an organisation of the surfactant molecules in the form of a bidimensional crystalline network. The form of these vesicles is anisotropic and is most often in the form of small faceted crystals. In every case, the size of these vesicles is between 0.1 and 50 $\mu$m. The faceted aspect of these vesicles is not contradictory with their onion type multilamellar structure.

According to a variant of the invention, as set forth above, it is possible to coat the microcapsules described above with a cross-linked polymer which enables improving the qualities of the capsules formed.

It is also possible to encapsulate, by the method described above, a cross-linking agent with a polymer which is absorbed onto the capsules. This operation can be carried out by incorporating calcium salt which acts as cross-linking agent in water which enables forming the capsules. By diluting these capsules in an alginate solution it is also possible to form multilamellar capsules coated with polymer (alginate) cross-linked by calcium. This enables limiting the leakage of a hydrophilic product and stabilising the microcapsules.

Another method consists in co-encapsulating by the method described above a polymer capable of being cross-linked by a chemical agent, an alginate for example. The dispersion of the capsules in a solution of the cross-linking agent (for example in the case of alginate, a calcium salt solution) leads, by diffusion of the cross-linking agent inside the capsules, to the cross-linking of the encapsulated polymer. Capsules are thus obtained which are solidified by the incorporation of a cross-linked polymer, which reduces considerably the leakage of the active principle.

Other natural polymers can also be used to this end. Guar gum can be cited, the cross-linking agent of which is borax, pectin, cross-linked by $Ca^{++}$ ions, or carrageenans, cross-linked according to their type by potassium or calcium ions.

EXAMPLES

The examples that follow illustrate the present invention. Example 19 is given with reference to the sole FIGURE which represents, in a semi-log scale, the variations in the intensity of fluorescence of a probe having crossed a skin barrier (reconstructed human epidermis), in the free form or in the encapsulated form.

Example 1

Preparation of lecithin/sucroester microcapsules 10 g of sucrose monopalmitate marketed by RYOTO under the trademark P1570 or P1670 are mixed with 50 g of water in a conical flask at 60° C. The complete dissolution is allowed then, 40 g of soya lecithin are added marketed under the trademark Mactan P97 by NORTE, which are mixed in the hot. The temperature is allowed to reach ambient temperature. A homogeneous paste is obtained which can be easily dispersed either in water by simple stirring, or in a hydrophobic medium such as oil. It is possible to observe under the microscope the presence of spherical particles which correspond to the multilamellar vesicles. The dispersion in water remains stable and homogeneous with time. In contrast, the dispersion in oil is destabilised by flocculation of the vesicles which precipitate but can be simply re-dispersed by mechanical stirring.

Example 2
Preparation of sucroester/monoglyceride microcapsules 10 g of a mixture of mono- and di-glycerides marketed by WITCO under the trademark ATMOS 200 and 40 g of sucrose monopalmitate marketed by RYOTO under the trademark P1570 or P1670 and 50 g of water are introduced into a conical flask. Mixing is carried out in the hot (60° C.), cooling is then allowed with stirring to ambient temperature. A homogeneous paste is obtained which can be simply dispersed in water by simple stirring. It is possible to observe under the microscope the presence of spherical particles which correspond to multilamellar vesicles.

Example 3
Encapsulation of food colouring agents 10 g of sucrose monopalmitate marketed by RYOTO under the trademark P1570 or P1670 and 50 g of water in which 1 g of food colouring agent (E124) have already been dispersed, are mixed in a conical flask at 60° C. Complete incorporation is allowed, 40 g of lecithin are then added, which are mixed in the hot. The temperature is allowed to attain ambient temperature. A coloured homogeneous paste is obtained, which can easily be dispersed in water by simple stirring. It is possible to observe under the microscope the presence of spherical particles, which correspond to the multilamellar vesicles. A part of the capsules can be separated by centrifugation. Thus, it is verified by recovering the highly coloured capsules that the colouring agent, although hydrophilic, remains trapped within the capsules.

Example 4
Encapsulation of mint flavour 10 g of a mixture of mono- and di-glyceride marketed under the trademark ATMOS 300 by WITCO, 90 g of sucrose monopalmitate marketed by RYOTO under the trademark P1570 or P1670, 40 g of mint flavour and 60 g of water are introduced into a conical flask. Mixing is carried out in the hot (60° C.), then, cooling is allowed with stirring to ambient temperature. A homogeneous paste is obtained which can easily be dispersed in water by simple stirring. This paste can be used directly in preparations. It is possible to observe a remanence effect of the flavour by leaving an aqueous solution of this flavour to evaporate for example and comparing the encapsulated flavour to a non-encapsulated flavour solution.

Example 5
Encapsulation of fruit flavour 10 g of sucrose monopalmitate marketed by RYOTO under the trademark P1570 or P1670 and 30 g of water are mixed in a conical flask at 60° C. Complete dissolution is allowed, 40 g of lecithin and 20 g of fruit flavour are then added, which are mixed at 40° C. The temperature is allowed to attain ambient temperature. A coloured homogeneous paste is obtained, which can easily be dispersed in water by simple stirring. It is possible to observe under the microscope the presence of spherical particles, which correspond to the multilamellar vesicles.

Example 6
Fruit flavour/hydrogenated sucroglyceride capsules 50 g of hydrogenated sucroglyceride marketed by RHONE-POULENC under the trademark CELYNOL PPH, 38 g of water and 12 g of fruit flavour are placed in a beaker. Heat is given at 60° C. mixing and stirring is continued for 20 minutes. Cooling is then allowed. A paste of concentrated capsules containing the flavour is obtained. These capsules are dispersible in water with strong stirring.

Example 7
Fruit flavour/sucroglyceride/sucroester capsules 25 g of sucroglyceride marketed by RHONE-POULENC under the trademark CELYNOL LMO, 25 g of P1670 (from RYOTO), 38 g of water are place in a beaker. Heat is given at 60° C. in mixing and stirring is continued for 20 minutes. Cooling is then allowed. When the temperature attains 40° C., 12 g of flavour can be added. Stirring is continued for 30 minutes, then cooling is carried out. A paste of concentrated capsules containing the flavour is obtained. These capsules are dispersible in water with strong stirring.

Example 8
Sodium stearoyl-2-lactylate/sucroglyceride capsules containing fruit flavour 30 g of sodium stearoyl-2-lactylate marketed by WITCO under the trademark EMULSILAC S, 20 g of hydrogenated sucroglyceride marketed by RHONE-POULENC under the trademark CELYNOL PPH, 38 g of water and 12 g of fruit flavour are placed in a beaker. Heat is given at 60° C. in mixing, and stirring is continued for 20 minutes. Cooling is then allowed. A paste of concentrated capsules containing the flavour is obtained. These capsules are dispersible in water with strong stirring.

Example 9
Microcapsules from a non-aqueous solvent 40 g of lecithin, 10 g of sucrose monopalmitate marketed under the trademark P1670 by RYOTO, 50 g of glycerol are placed in a beaker. Heat is given at 60° C. with stirring for 30 minutes. Cooling is then allowed. A paste of capsules without water is obtained.

Example 10
Microcapsules containing a spice used in meat products

Microcapsules similar to those of Example 1 are prepared from 15 g of sucrose monopalmitate P1670, 35 g of soya lecithin, 45 g of water and 5 g of artificial sausage flavour obtained from 1-octen-3-ol. The paste obtained is dispersed in water in order to make dispersions containing 1%, 0.1% and 0.01% of flavour. These dispersions are used at the rate of 10 g of dispersion per kg of meat for manufacturing sausages. A sensory analysis shows that the sausages manufactured by incorporating the 0.1% flavour dispersion has a pronounced salted meat taste, whereas a control without flavour has not yet developed this taste.

Example 11
Microcapsule based on sucrose ester and monoglyceride 5 g of commercial sunflower oil monoglyceride and 7.5 g of vitamin E acetate are introduced into a 100 cm3 conical flask. The mixture is homogenised with mechanical stirring. When the paste is homogeneous, 20 g of commercial sucrose palmitate are added slowly with stirring, 17.5 g of water are then added. The product is homogenised under strong stirring at ambient temperature for at least 30 minutes, and then heated at 65° C. for 1 to 2 hours. After cooling with stirring, a concentrated phase is obtained formed from microvesicles according to the invention, that can be dispersed with stirring by the slow addition of the same volume of water. Observation under the optical microscope shows a dense population of microvesicles of size ranging from 0.5 to several micrometers.

Example 12
Microcapsules containing a crosslinked polymer

A 0.5% sodium alginate solution is prepared by dispersing the powdered polymer under strong stirring in water at ambient temperature, and then leaving it under stirring for one hour. 5 g of sunflower oil monoglyceride (DIMODAN LS, GRINDSTED) and 7.5 g of vitamin E acetate are introduced into a 100 cm3 conical flask. The mixture is homogenised with mechanical stirring. When the paste is homogeneous, 20 g of sucrose palmitate are added slowly with stirring, and then 17.5 g of the sodium alginate solution prepared above are added. The product is homogenised under strong stirring at ambient temperature for at least 30 minutes, then heated at 65° C. for 1 to 2 hours. After cooling with stirring, a concentrated phase is obtained formed from microvesicles which are dispersed with stirring by the slow addition of the same volume of a 0.5% aqueous solution of CaCl2. Observation under the optical microscope of the dispersion shows the vesicles containing the crosslinked polymer, which can be separated by centrifugation and show a high rigidity.

Example 13
Microcapsules containing a crosslinked polymer

A 1% solution of guar gum is prepared by dispersing the powdered gum with strong stirring in water at ambient temperature, and then leaving it under stirring for one hour. This solution is used in a preparation identical to that of Example 12. The paste formed from the vesicles is dispersed in a 1% aqueous solution of sodium borate. Microvesicles encapsulating the crosslinked polymer are thus obtained.

Example 14
Microcapsules of sucrose ester and glyceride

The method is identical to that of Example 11 but with the following proportions:
sucrose palmitate: 15 g
sunflower oil monoglyceride: 7.5 g
vitamin E acetate: 5 g
hydroglycolic extract of flowers (corn flower, camomile, lime-tree flowers) 22.5 g (instead of water).

The paste obtained at the end of the preparation is dispersed in three times its volume of water so as to obtain a milky fluid dispersion of microvesicles.

Example 15
Microcapsules of sucrose ester and glyceride

The method is identical to that of Example 11, but with the following proportions:
sucrose palmitate 17.5 g
sunflower oil monoglyceride: 5 g
vitamin E acetate: 5 g
aqueous extract of marine α-hydroxyacids: 22.5 g The dispersion in the same volume leads to a cream which contains the α-hydroxyacid microvesicles of pH around 4.

Example 16
Composition for deodorant 22.5 g of sucrose palmitate, 5 g of vitamin E acetate, 3 g of commercial 2,4,4'-trichloro-2'-hydroxybiphenylether, 10 g of perfume base for deodorant and 9.5 g of water are introduced into a 100 cm3 conical flask. The mixture is homogenised under strong stirring at ambient temperature, heat is then given at 65° C. with stirring for at least one hour. After cooling with stirring, a paste containing the microvesicles of the invention is obtained. This paste is introduced with stirring into a solid body deodorant preparation in the form of an aqueous stearate gel, commonly designated as a <<stick>>. A body deodorant <<stick>> is thus obtained which contains the microvesicles encapsulating the perfume and the bactericide.

Example 17
Sucrose ester based microcapsules 15 g of sucrose monostearate and 35 g of water are introduced into a 100 cm3 conical flask. The mixture is homogenised under strong mechanical stirring at ambient temperature for at least 30 minutes and is then heated at 65° C. for 1 to 2 hours under strong stirring. After cooling, a concentrated cream is obtained which contains the microvesicles, which can be dispersed both by the slow addition of water with mechanical stirring, and by the slow addition of a vegetable oil under the same conditions. The dispersion in oil possesses a tendency to precipitate due to the lower efficiency of the Brownian motion in this medium.

Example 18
Microcapsules based on sucrose ester 20 g of sucrose stearate and 5 g of sucrose palmitate are introduced into a 100 cm3 conical flask. 50 g of water are added slowly with stirring. The mixture is homogenised under strong mechanical stirring at ambient temperature for at least 30 minutes and is then heated at 65° C. for 1 to 2 hours. After cooling, a concentrated cream is obtained which contains the vesicles of the invention.

Example 19

A preparation of fluorescent microvesicles is carried out according to the method of Example 11, from the following materials:
sucrose palmitate: 20 g
sunflower oil monoglyceride: 5 g
vitamin E acetate: 7.5 g
fluorescein dilaurate: 0.5 g
water: 17 g The concentrated microvesicle paste is dispersed at 1% in water. This dispersion is tested for its capacity to cross a reconstructed human epidermis, compared to the same concentration of fluorescent probe dissolved in di(ethylenglycol) ethyl ether (TRANSCUTOL).

The test is effected on a cell model (EPISKIN, SADUC) of reconstructed human skin. The solution under study is a 10% solution of the preceding dispersion or a 10% aqueous dilution of the fluorescein dilaurate solution in transcutol. The probe concentration is therefore $10^{-5}$. The test is carried out in triplicate over 48 hours, and the passing of the probe is measured by fluorescent spectroscopy after visualisation of the fluorescent of the probe in basic medium. The results are summarised on the graph in the single FIGURE, which represents the fluorescent intensity against time on a semi-log scale. It is noted that the very clear acceleration of the kinetics of the passage of the microvesicles with respect to the free probe. A cytotoxicity test is carried out at the end of the experiment, following a protocol which uses dimethylthiazoldiphenyltetrazolium bromide (MTT), using the MTT kit from Saduc. It shows a slight cytotoxicity of the free probe at 48 hours, which disappears in the encapsulated probe. This effect is to be correlated with the acceleration of the passage of the free probe at 48 hours, which does no longer appear on the encapsulated probe.

We claim:

1. An active principle carrier having the form of multilamellar vesicles constituted of concentric membranes, said membranes comprising at least one non-ionic surfactant of the sucrose ester type that comprises at least one $C_{12}$–$C_{22}$ fatty acid chain, said fatty acid chain being selected from the group consisting of linear saturated chains, linear unsaturated chains, branched saturated chains and branched unsaturated chains, the fatty acid chains optionally being substituted with one or more hydroxyl groups.

2. The carrier according to claim 1, wherein said fatty acid is a fatty acid of natural origin.

3. The carrier according to claim 1, further comprising at least one other surfactant.

4. The carrier according to claim 1, wherein said fatty acids are selected independently from the group consisting of lauric acid, myristic acid, palmitic acid, stearic acid, behenic acid, oleic acid, linoleic acid, linolenic acid, arachidonic acid, ricinoleic acid and mixtures thereof.

5. The carrier according to claim 1, wherein said vesicles are constituted of a multilamellar arrangement of concentric bi-layers comprising at least one ester-type surfactant that are separated by an interstitial solvent comprising a polar liquid.

6. The carrier according to claim 1, wherein said vesicles have dimensions between 0.1 and 50 μm.

7. The carrier according to claim 1, wherein the members of said vesicles comprise a mixture of at least two surfactants at least one of which is a surfactant of the sucrose ester type as defined in claim 1, said surfactants comprising a first lipophilic surfactant, having a hydrophilic-lipophilic balance (HLB) between 3 and 7, and a second hydrophilic surfactant, having an HLB between 8 and 15.

8. The carrier according to claim 7, wherein at least one of the surfactants has a critical micellar concentration (CMC) lower than $10^{-5}$ mol/l.

9. The carrier according to claim 7, wherein the lipophilic surfactant is present in proportions expressed in percentages by weight with respect to the whole of the surfactants between 20 and 100%.

10. The carrier according to claim 1, wherein said vesicles contain at least one surfactant belonging to the family of fatty acid sucroesters derived from vegetable fats.

11. The carrier according to claim 1 wherein said vesicles further comprise a polymer intended for reinforcing them, said polymer being either used for coating said vesicles, or encapsulated within them.

12. The carrier according to claim 11, wherein said polymer is selected from the following classes of polymers:

natural or modified, linear or substituted, neutral or ionic polysaccharides, gelatine, and hydro or liposoluble synthetic polymers.

13. A composition for use as food or diet food, comprising at least one active food or diet food product encapsulated in the vesicles constituting the carrier according to claim 1.

14. The composition according to claim 13, wherein said active product is selected from the group consisting of acid-type products for use as food.

15. A cosmetic or pharmaceutical composition, comprising at least one active cosmetic or pharmaceutical principle encapsulated in the vesicles constituting the carrier as defined according to claim 1.

16. The carrier according to claim 1, wherein said ester further comprises at least one carboxylic chain from an acid compound selected from the group consisting of saturated $C_2$–$C_4$ mono acids, unsaturated $C_2$–$C_4$ mono acids, saturated $C_2$–$C_4$ polyacids, unsaturated $C_2$–$C_4$ polyacids, and derivatives of the $C_2$–$C_4$ acids substituted with one or more hydroxyl groups that optionally are esterified with acetic acid.

17. The carrier according to claim 1, wherein the ester is in a mixture with a mono-, di-, or tri- ester of glycerol with a $C_{12}$–$C_{22}$ fatty acid selected from the group consisting of linear saturated fatty acids, linear unsaturated fatty acids, branched saturated fatty acids, branched unsaturated fatty acids and derivatives of the fatty acids substituted with one or more hydroxyl groups.

18. A method for preparing a composition comprising an active product according to claim 1, comprising:

preparing a lamellar crystal liquid phase comprising a mixture of at least one surfactant including a non-ionic surfactant of the sucrose ester-type as defined in claim 19, a polar solvent and the active product to be encapsulated; and transforming said lamellar crystal liquid phase into vesicles.

19. The carrier according to claim 2, wherein the fatty acid is of plant origin.

20. The carrier according to claim 16, wherein the $C_2$–$C_4$ acid or derivative thereof is selected from the group consisting of acetic acid, lactic acid, citric acid, tartaric acid, acetyltartaric acid and succinic acid.

21. The carrier according to claim 3, wherein the other surfactant is selected from the group consisting of lecithin, a sorbitan ester, and a polysorbate.

22. The carrier according to claim 6, wherein the dimensions of said vesicles are between 0.2 and 10 μm.

23. The carrier according to claim 8, wherein the critical micellar concentration is lower than $10^{-6}$ mol/l.

24. The carrier according to claim 12, wherein the polymer is selected from guar gums, locust bean gums, gum arabic, carrageenans (kappa, iota, and lambda), xanthan gums, natural, esterified and amidated pectins, alginic acid and salts thereof, hyaluronic acid, quaternized guar gums and chitosan and substituted derivatives thereof.

25. The carrier according to claim 12, wherein the polymer is selected from the group consisting of polyacrylamide, polyvinylpyrrolidone, and polyethylene glycol.

26. The composition according to claim 14, wherein the active product is selected from the group consisting of ascorbic acid, lactic acid, coloring agents, food flavors, lipids, vitamins, essential oils and enzymes.

* * * * *